United States Patent [19]
Columbus et al.

[11] Patent Number: 5,171,532
[45] Date of Patent: Dec. 15, 1992

[54] CENTRIFUGE-CONTAINING ANALYZER

[75] Inventors: Richard L. Columbus, Rochester; Johannes J. Porte, Webster, both of N.Y.

[73] Assignee: Eastman Kodak Company, Rochester, N.Y.

[21] Appl. No.: 527,797

[22] Filed: May 22, 1990

Related U.S. Application Data

[63] Continuation-in-part of Ser. No. 484,014, Feb. 23, 1990, abandoned.

[51] Int. Cl.⁵ .............................................. G01N 9/30
[52] U.S. Cl. ..................................... 422/72; 422/100; 436/45
[58] Field of Search ............... 210/789, 745; 422/106, 422/72, 100; 436/45, 48

[56] References Cited

U.S. PATENT DOCUMENTS

| 3,175,762 | 3/1965 | Dinter, Jr. .............................. 233/11 |
| 3,635,394 | 1/1972 | Natelson ................................ 233/26 |
| 4,927,545 | 5/1990 | Roginski ................................ 422/106 |

FOREIGN PATENT DOCUMENTS

| 299519 | 1/1989 | European Pat. Off. . |
| 60-237368 | 11/1985 | Japan . |

Primary Examiner—Jill A. Johnston
Attorney, Agent, or Firm—Dana M. Schmidt

[57] ABSTRACT

An analyzer features an incubator and a whole blood centrifuge, each using a separate rotor, and a serum-dispensing station in between them. A transfer mechanism is also included for moving a container used in the rotor to separate serum from blood cells, out of the rotor to the dispensing station. The serum is then dispensed directly from such container onto a test element, which is transferred to the incubator.

6 Claims, 7 Drawing Sheets

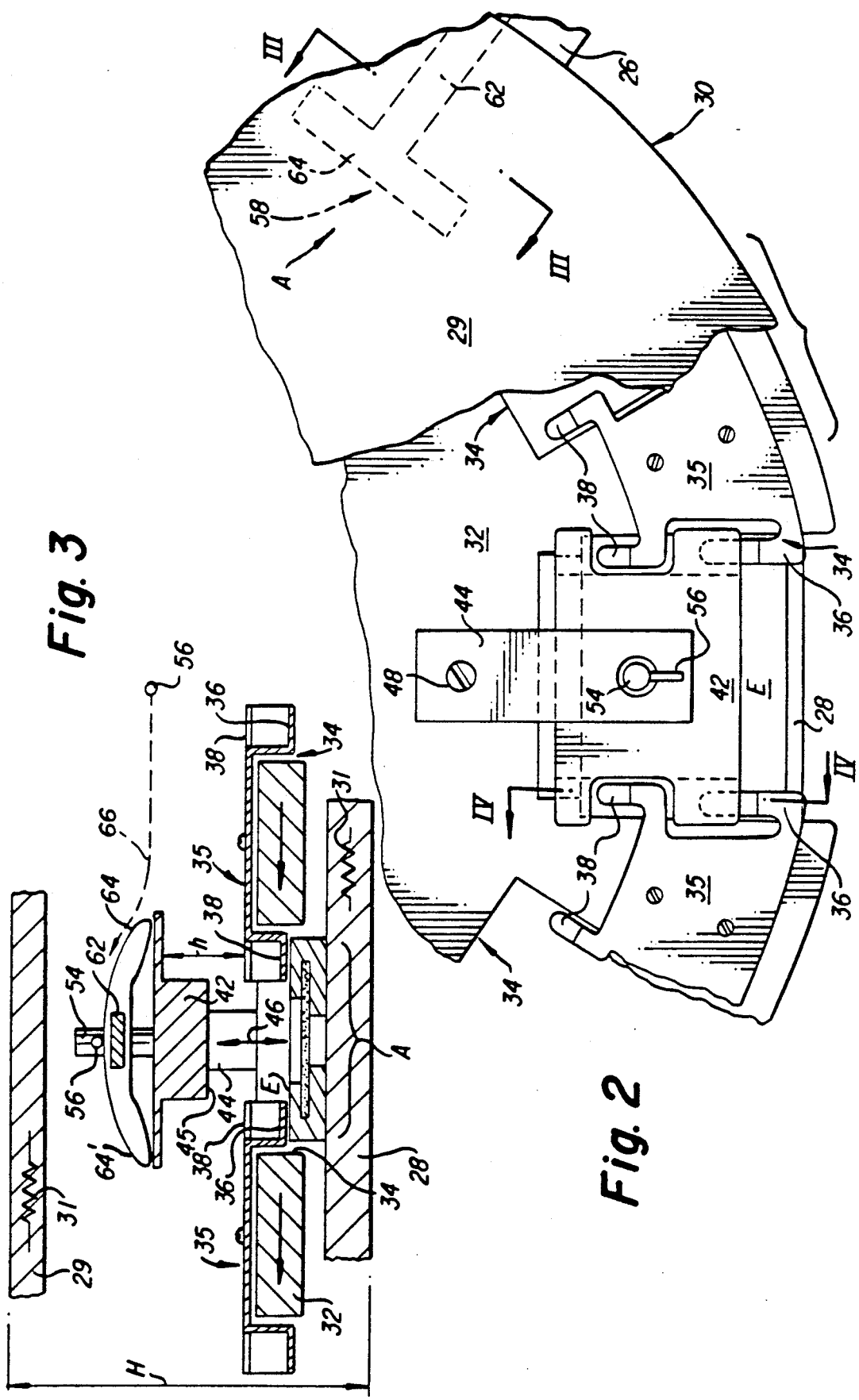

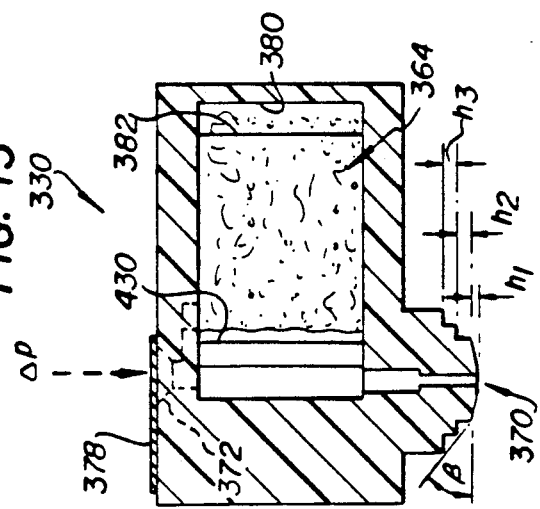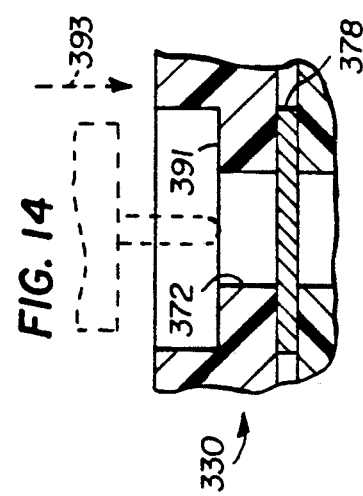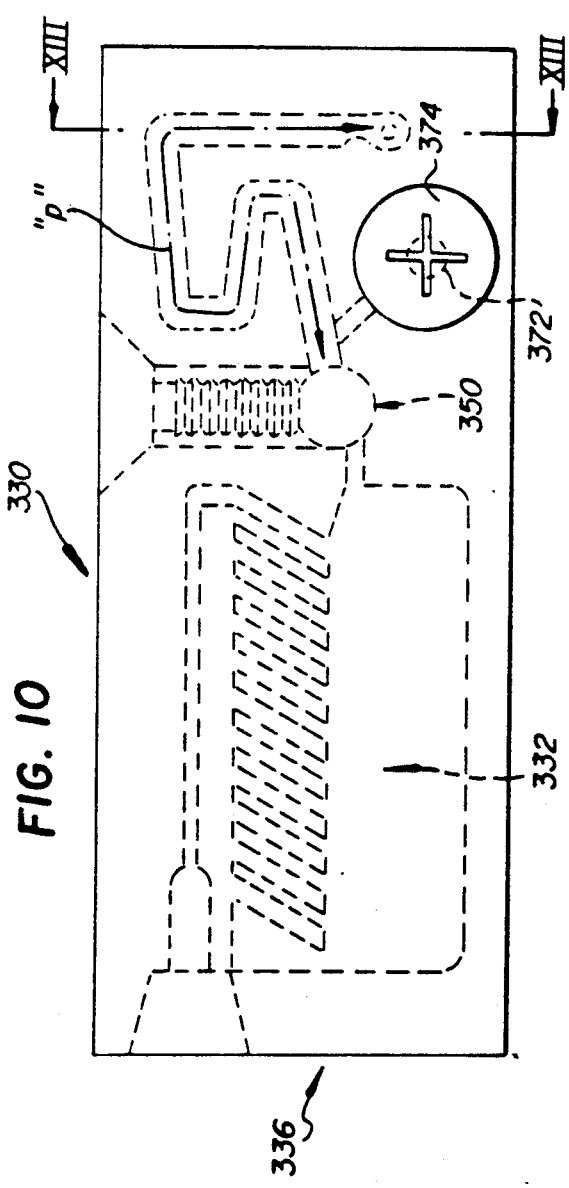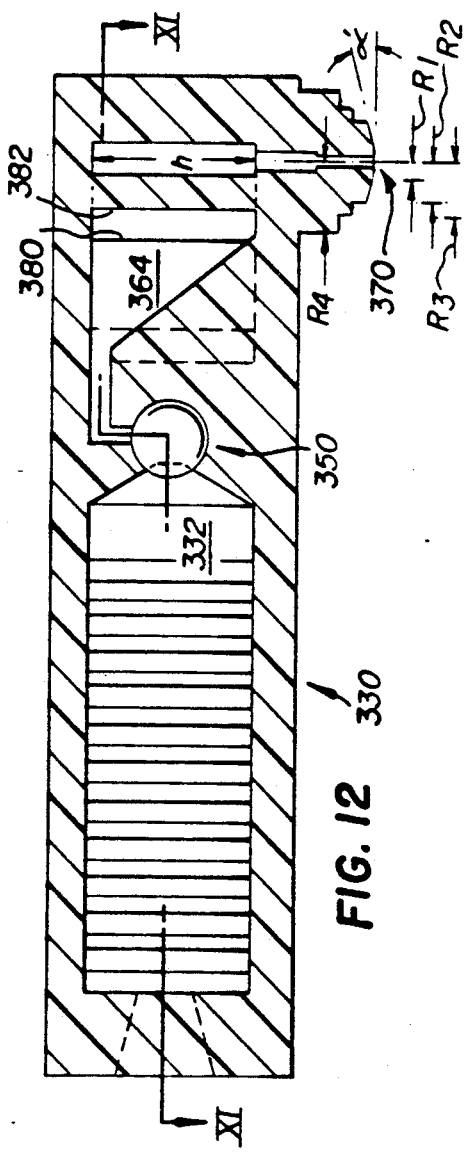

CENTRIFUGE-CONTAINING ANALYZER

This is a continuation-in-part of application Ser. No. 07/484,014, filed Feb. 23, 1990 and now abandoned.

1. FIELD OF THE INVENTION

The invention relates to blood analyzers used to assay for analytes of blood, and specifically one which receives whole blood for testing.

2. BACKGROUND OF THE INVENTION

In the processing of whole blood to test for analytes, the conventional approach generally has been to spin the whole blood in a stand-alone centrifuge, and then pour-off separated serum into a new container to be tested in an analyzer separate from the centrifuge. The analyzer in turn may use a rotor in its incubator. To consolidate instruments, an analyzer has been constructed that provides for a rotating incubator that also doubles as a centrifuge. Such a device is shown in Japanese Kokai 85/237368. Although this construction avoids the necessity of separate rotors performing the separate functions of centrifuging and incubating, it does incur some significant disadvantages. They are as follows:

a) Since the incubator rotor necessarily holds the spin container as well as the test element, a transfer mechanism is provided to transfer serum after separation from the spin container to that test element and ONLY to that test element. As a result, all the blood collected is dedicated to a single test element, which in this publication (and in general use) is a slide-like element. This is a substantial waste, since the usual practice is to collect 10 ml or so of blood but to dispense only a 10 $\mu$L drop on each slide-like test element. Of course, one could draw out only a micro-amount, say 100 $\mu$L, of blood and place that in the rotor to be spun, but this would necessitate a large number (X) of micro-containers to be placed in the phlebotomy syringes in succession, to run X different assays on a single patient. Such a large number of insertions and removal from the syringe would unduly tax the phlebotomist assigned to blood collection duties.

b) Still further, any design that forces the incubator rotor to double as a centrifuge will require precision manufacturing and assembly of the stations of the rotor to insure the proper balancing of the rotor during high speed rotation. Since the incubator rotor has to perform other features as well, such as temperature control, and in some cases, detection of reactions due to the analyte while still in the incubator, it becomes difficult to make the incubator rotor perform in this manner.

Thus, a more convenient construction would be one in which the centrifuge comprises a rotor in the analyzer that is separate from the rotor of the incubator, so that the centrifuge rotor need perform only ONE function well—that of spinning at high speed. Nevertheless, the prior art has not provided for such two separate rotors in the same analyzer, TOGETHER with automatic means for transferring separated serum from the centrifuge rotor to a test element that is then transferred to the incubator rotor. One reason may well be that most centrifuge rotors spin about a vertical axis, necessitating vertical loading and unloading, which does not accommodate readily to most analyzers which have a generally horizontal flow of materials through the work stations.

In any event, prior to this invention the marriage of the centrifuge and the incubator has not been taught in an automated way, without making the marriage so complete that it forces the incubator to also be the centrifuge, thus performing too many disparate functions.

SUMMARY OF THE INVENTION

I have constructed an analyzer that solves the above-noted problems.

More specifically, there is provided a blood analyzer comprising an incubator, a test element support, a serum dispensing station positioned adjacent to the incubator to dispense serum onto a test element disposed on the support, and means for moving a test element spotted with the dispensed serum from the dispensing station into the incubator. This analyzer is improved in that the analyzer further includes a centrifuge disposed adjacent to the dispensing station and separate from the incubator, the centrifuge including a station spaced from an axis and constructed to hold a container of whole blood for spinning about the axis to separate serum from blood cells, means for moving a spun container from one of the centrifuge stations to the dispensing station at a location spaced from the support, and further including means at the dispensing station for dispensing serum from the container to a test element on the support.

Accordingly, it is an advantageous feature of the invention that a centrifuge is incorporated into an analyzer without requiring it to also function as an incubator.

It is a related advantageous feature of the invention that such an analyzer avoids the cumbersome transfer mechanisms, and the height associated therewith, necessitated when using a vertically oriented centrifuge.

Other advantageous features will become apparent upon reference to the following Description of the Preferred Embodiments, when read in light of the attached drawings.

Brief Description of the Drawings

FIG. 2 is a fragmentary, enlarged plan view similar to that of FIG. 1, showing the incubator in greater detail;

FIG. 3 is a section view taken generally along the line III—III of FIG. 2;

FIG. 10 is a plan view of an alternate form of the container in FIG. 5;

FIG. 12 is a section view taken generally along the line XII—XII of FIG. 11;

FIG. 13 is a section view of the device of FIG. 10 taken generally along the line XIII—XIII of FIG. 10 and showing in phantom the connection of the air pressure aperture with the second chamber; and FIG. 14 is an enlarged fragmentary view in section of an alternate embodiment of the pressurizing of the second chamber.

DESCRIPTION OF THE PREFERRED EMBODIMENTS

The invention is described in connection with the preferred embodiments, featuring a preferred incubator and a preferred serum-separating container. In addition, the invention is useful regardless of the design of the specific rotor of the incubator, and regardless of the design of the container for separating and delivering serum, provided the noted container is amenable to centrifugation and serum dispensing.

Figure 1:
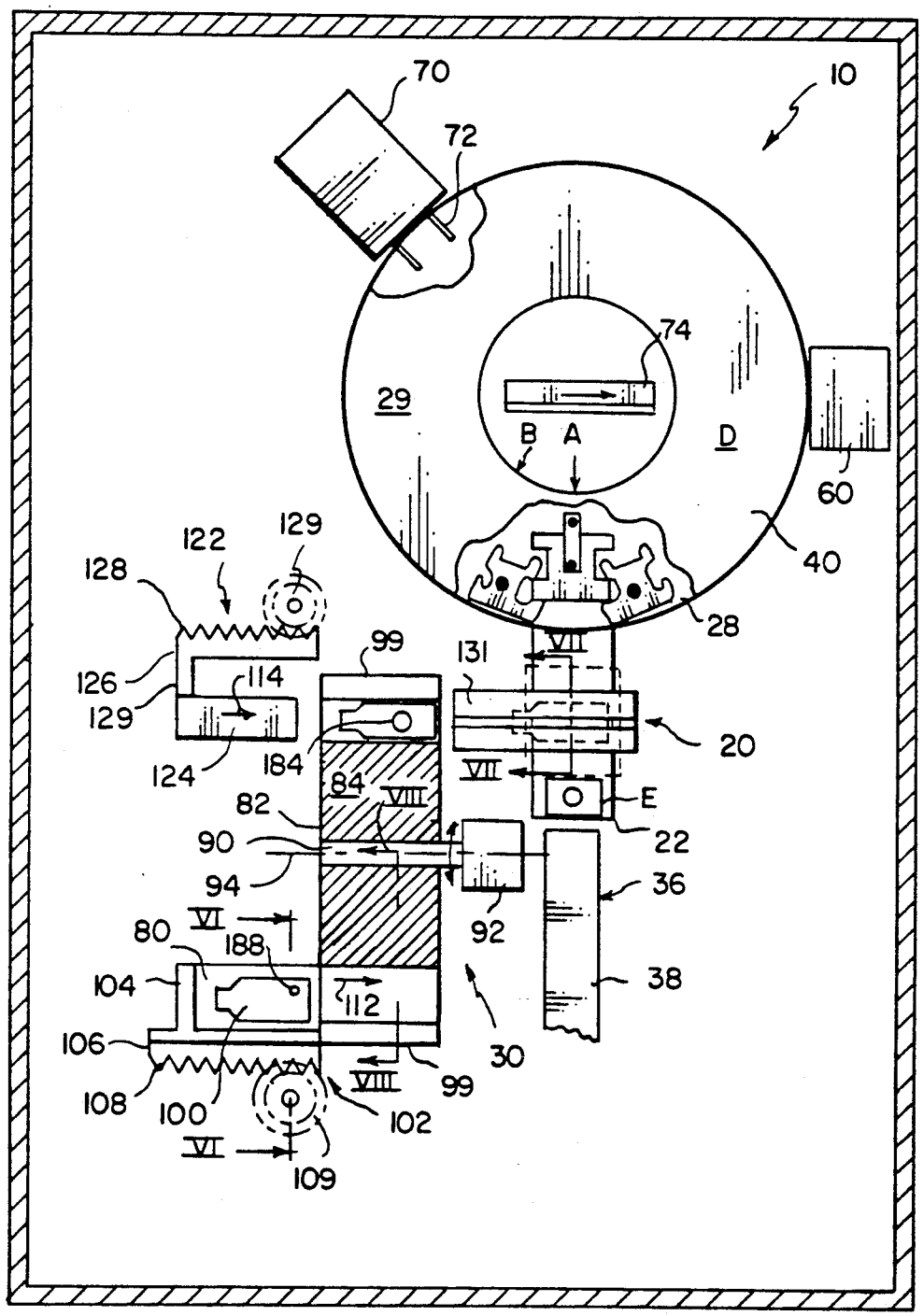
FIG. 1 is a plan view, partly in section, of an analyzer constructed in accordance with the invention.

Referring first to FIG. 1, an analyzer 10 useful with the invention preferably comprises a serum dispensing station 20, means 30 for supplying serum to the serum dispensing station 20, incubator 40, means 36 for supplying test elements E to station 20 and then to the incubator, and reading stations 60 and 70 for detecting changes in test element E due to analytes present in the patient sample. Preferably, the test elements are so-called dried slide-like elements, particularly those available from Eastman Kodak Company under the trademark "Ektachem"; although other dried test elements are also useful.

Except for the means 30 for supplying serum to station 20, described hereinafter, analyzer 10 and the aforementioned stations and components are conventional. Briefly, elements E are moved into position onto a support 22 from a suitable supply, not shown, using a pusher blade 38 driven by a suitable motor (not shown), or by some other transfer mechanism. Element E, which can be either a colorimetric or a potentiometric element, is then pushed into station 20 by blade 38, where serum is dispensed as is more clearly shown in FIG. 7, described below. Thereafter, element E is pushed again by blade 38 into incubator 40.

As is described more fully in commonly owned U.S. Serial No. 293,718 filed Jan. 5, 1989 by H. Porte entitled "Incubator and Analyzer with Improved Cap Raising Means", now U.S. Pat. No. 5,034,191 incubator 40 preferably comprises a stationary lower support plate 28, FIGS. 2-3, and a stationary upper cover plate 29. Either or both of these plates are heated by elements 31, FIG. 3, in a conventional manner with sensors, not shown, to provide feedback to control the incubator temperature as desired. Mounted between plates 28 and 29, FIGS. 2 and 3, is a rotor 32 providing individual test-element holding stations formed as pockets in the rotor. More specifically, indentations 34 are formed in rotor 32, and hold-down leaf springs 35 are attached along the periphery of each indentation. The indentations are shaped and sized to hold a test element E therein, and springs 35 are shaped to press a test element against lower support plate 28, FIG. 3. Preferably, springs 35 are dual springs that extend over the top of rotor 32, with a pair of fingers 37, 39 adjacent each indentation 34. Additionally, an evaporation cap 42 is provided, FIGS. 2 and 3, that is attached via a leaf spring 44 to rotor 32 to permit limited vertical movement, FIG. 3, arrow 46, of cap 42. Spring 44 is attached at 48 to rotor 32, FIG. 2. Undersurface 45 of cap 42 seals against test elements E.

Means are provided for raising cap 42 against the action of spring 44 in a passive, rather than active way, simply by moving rotor 32 either into load station A or unload station D, FIG. 1. More specifically, FIGS. 2 and 3, each cap 42 has a rod 54, and projecting from rod 54 a cam follower pin 56 that functions as described below.

To raise cap 42 when rotor 32 moves an indentation 34 on plate 28 to station A to receive a test element, FIGS. 2 and 3, cam 58 is provided at station A, shown in phantom in FIG. 2. Cam 58 comprises a fixed bridge element 62 fixed to the analyzer and having an arcuate ramp surface 64. The shape of surface 64 is constructed to cam pin 56 upward, and thus raise cap 42, as shown by arrow 66, FIG. 3. Surface 64 spans the load station A, FIG. 3, and is fixed in place between the upper and lower heated plates 28 and 29. Distance "h" that cap 42 is raised is the distance sufficient for moving a test element into or out of place at indentation 34, without causing liquid protruding from the element to strike undersurface 45 of cap 42. For example, distance "h" can be 4 mm. The same is true regardless whether test element E is a potentiometric or colorimetric element.

When pin 56 traverses down the "down" side 64' of surface 64, cap 42 is lowered back into sealing contact with test element E, by reason of spring 44.

The construction of cam 58 at station D (not shown) is substantially identical with its construction at station A.

Station 60 is a colorimetric read station while 70 is a potentiometric read station. Both are conventional, so that no further description is required. A pusher blade 74 is useful in ejecting a test element, after incubation, from incubator 40 into station 60. On the other hand, probes 72 of read station 70 can be used to read a potentiometric element while it is in the incubator.

Figure 6:
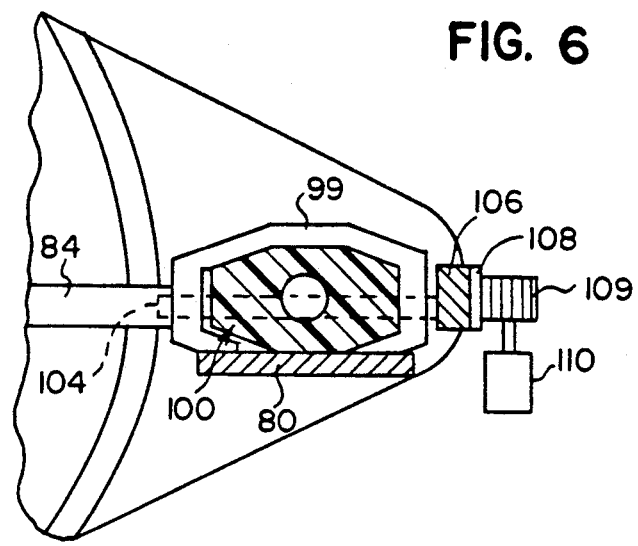
FIG. 6 is a fragmentary elevational view in section taken generally along the line VI—VI of FIG. 1.

In accordance with the invention, the patient sample liquid supplied to an analyzer 10 is whole blood, not serum, because the analyzer has the built-in capability of separating the serum in situ. However, unlike the prior art, it does not attempt to do this using the incubator rotor. Referring more specifically to FIGS. 1 and 6, means 30 for supplying serum comprise a platform 80 for receiving a container 100 of whole blood, a centrifuge 82 for spinning container 100 to separate the blood into serum and cells, means 102 and 122 for automatically moving containers 100 into and out of the centrifuge respectively, and means 120, FIG. 7, for pressurizing the container to dispense only separated serum.

More specifically, horizontal platform 80, FIG. 1, is stationarily positioned to receive a container 100 that is manually or otherwise placed into the analyzer through an appropriate opening. Centrifuge 82 comprises a rotor 84 having a center hub 86, FIG. 8, attached to a drive shaft 90 driven by a motor 92 about an axis 94. Rotor 84 includes radially extending arms that terminate in stations 99 that are disposed around the rotor circumference, as is conventional. However, to minimize transfer complexities and height of the analyzer, axis 94 is disposed parallel to the main plane of flow of containers 100, namely it is disposed to be horizontal rather than the more usual vertical orientation. Stations 99 can be of a variety of designs, and preferably are such as to snugly receive containers 100 and to hold them during spinning. The details of containers 100 are set forth hereinafter.

To minimize the inertia of the centrifuge and thus the power needed to drive it, the rotor arms carrying stations 99 are kept as thin as possible, so that most of the mass of the rotor is kept close to axis 94.

With regard to moving means 102 and 122, FIG. 1, these can have a variety of configurations. A preferred design comprises pusher members 104 and 124, respectively, which extend from one side of a frame member 106 and 126, respectively. The frame member in turn has, on its opposite side a rack gear 108 and 128, that cooperates with a pinion gear 109 and 129, driven by a suitable motor 110 and 130 (FIG. 6), respectively. Frame member 106 is disposed to move just above support 80, so that pusher member 104, shown shaped as a finger and shown in phantom, FIG. 6, can reciprocate horizontally above support 80 and contact and push container 100 off support 80, into centrifuge 82, arrow 112, FIG. 1. Pusher member 124, on the other hand, FIG. 1, is shaped as a pusher blade, of a width and length effective to be inserted into a station 99 of centrifuge 82 so as to push horizontally a spun container 100 completely out, arrow 114, and onto a support 131 disposed between centrifuge 82 and the adjacent dispensing station 20.

Figure 8:
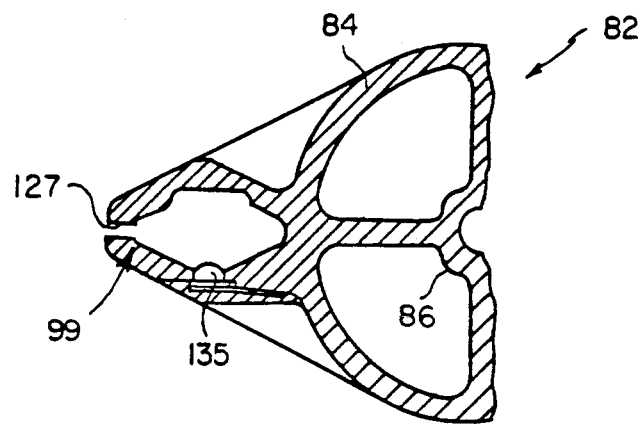
FIG. 8 is a fragmentary section view of the centrifuge rotor, taken generally along the line VIII—VIII of FIG. 1.

To allow member 124 to push container 100 fully out of rotor 84, stations 99 can be slotted at 127, FIG. 8, to accommodate connecting portion 129 of member 124, FIG. 1. In addition, a spring-loaded detent 135, FIG. 8, is optionally included to press against container 100 to hold it in a station. For example, detent 135 can bear against aperture 182 sealed by 184.

The movement of moving means 102 and 122 is of course coordinated with the non-rotation of the centrifuge. Rotor 92 is indexed as desired by the analyzer's computer (not shown) to line up the desired stations.

Figure 4:
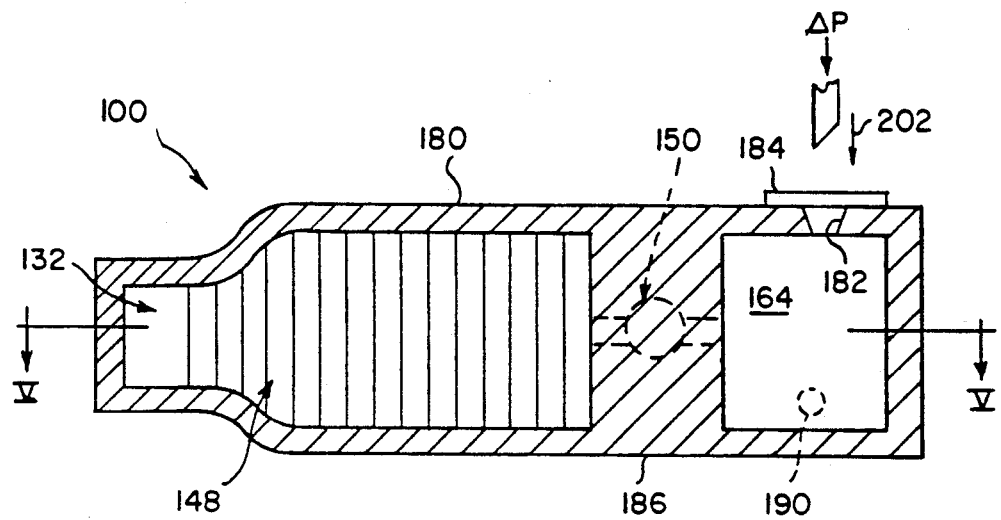
FIG. 4 is a section view of a container taken generally along the line IV—IV of FIG. 5.
Figure 5:
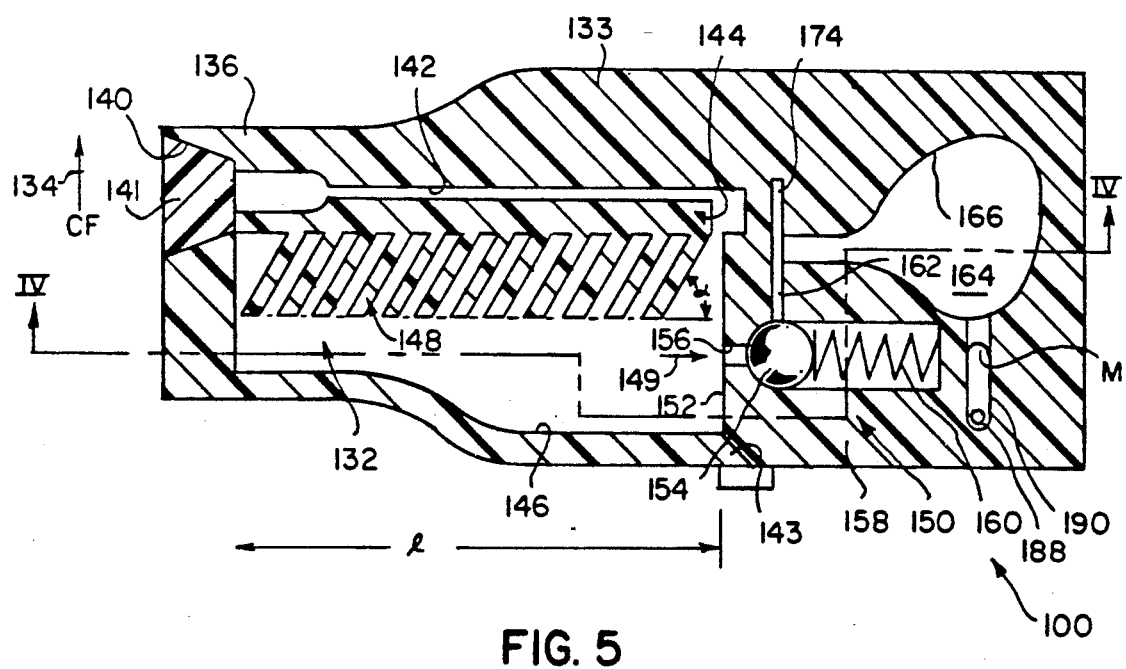
FIG. 5 is a section view of the container taken generally along the line V—V of FIG. 4.

Referring next to FIGS. 4 and 5, a preferred container 100 is one with two chambers 132 and 164, and a valve 150 disposed between them. As described in commonly owned U.S. Ser. No. 442,826 filed by Columbus et al. on Nov. 29, 1989 entitled "Blood Collection Device", now abandoned a useful container has the following features: chamber 132 for phase separation has its long dimension l oriented perpendicular, not parallel, to the direction of centrifugal force CF, arrow 134, and with a specially constructed valve 150. Chamber 132 is defined by a body member 133 having a blood intake end 136 and an opposite, serum-removal end 152. Chamber 132 extends from end 136 to delivery passageway 156. End 136 has an intake aperture 140 filled with a conventional septum 141, chamber 132 being either vented at 143 or evacuated due to attachment at 143 to an external vacuum source, to assist in blood intake. Aperture 140 allows entrance of whole blood via passageway 142 to chamber 132. Sidewall 144 of chamber 132 is the sidewall against which the heavier blood cells collect, whereas opposite sidewall 146 is adjacent the lighter serum fraction, during centrifugation.

Optionally, fixed porous mechanical means, such as baffles 148, can be positioned along wall 144 so as to be disposed in the blood cells. As described in commonly owned U.S. application Ser. No. 325,725 filed on Mar. 20, 1989 entitled, "Phase Separation Container with Fixed Means Preventing Remixing", such means act to retain the heavier phase from remixing when the lighter, serum phase is drawn off. The plates of the baffles are inclined at an angle alpha that resists remixing forces when flow occurs out of chamber 132 in the direction of arrow 149. Preferably, this angle is a value that is between about 30° C. and about 120° C., most preferably about 60° C. Preferably, the distance between the individual plates of baffles 148 is between about 0.018 cm and about 0.10 cm, most preferably about 0.025 cm. The thickness of each plate is not critical, so long as a significant number of such plates are present as will create the needed volume between them to collect the blood cells.

Valve 150 is disposed adjacent an end 152 of chamber 132, positioned to draw off separated, plasma or serum and lymphocytes (discussed hereinafter). Most importantly, valve 150 is constructed to open only in response to a hydraulic head of force, and not to the effects of force CF, regardless of the magnitude of the latter. To this end, valve 150 is preferably a ball check valve with a ball 154 positioned downstream of passageway 156 at chamber end 152. Ball 154 seats against a hemispherical seat 158, and is biased by a spring 160 aligned to act in a direction that is generally perpendicular to the direction of force CF. This alignment tends to ensure that ball 154 will act against spring 160 only in response to forces other than force CF.

A serum or plasma exit passageway 162 is constructed adjacent seat 158, to carry off the liquid when valve 150 opens. Passageway 162 joins a chamber or compartment 164 sized to receive substantially all the liquid that exits chamber 132 via valve 150. Chamber 164 has a deep well portion 166.

Passageway 162 preferably extends beyond chamber 164 to a trap 174. The function of the trap is to collect the few red blood cells that will gather prior to and during centrifuging, in passageway 156, allowing only desired serum, or plasma and lymphocytes, to pass into chamber 164.

Container 100 can be assembled as two plates, to achieve a seal that will allow a vacuum to be drawn using vent 143, as described above.

Such a container 100 can be spun with the long dimension l generally parallel to the spin axis 94, FIG. 1. Preferred spin radii are about 2.5 cm, although a wide variety can be used.

The method of phase separating, using container 100, will be readily apparent from the preceding discussion. Whole blood is placed into chamber 132 by, e.g., a needle that penetrates septum 141. Container 100 is then spun about axis 94, FIG. 1. However, the speed of rotation that is selected can be slow—a speed producing no greater than 400 g's centrifugal force, and most preferably not greater than 30 g's. The reason is that container 100 is capable of achieving phase separation at such forces, using 2 mL of liquid, in less than 2 minutes, and in some cases less than 1 minute, due to the (relatively) short distance that the blood cells have to traverse to be separated. Separation times achievable with the invention, using a 2.5 cm spin radius and a total whole blood volume of 500 μL, include separation in less than 1 minute if the centrifugal force is about 150 g's or greater, there being little separation time enhancement occurring at forces above 400 g's. At the other end, a separation force of only 30 g's will produce complete phase separation in less than 8 minutes, for example, 5.5 minutes. As a comparative example, as described in U.S. Pat. No. 4,818,418 the conditions achieved using a conventional Ficol-Pague/Percoll as an additive and a force of 400 g's, achieves separation only after 30 minutes.

Whatever centrifugal force that is selected, after serum or plasma separation occurs the lighter phase is then drawn off the stacked liquid in chamber 132, by opening valve 150. This occurs as follows: spring 160 has a spring constant $K_1$ that is pre-selected to resist movement of ball 154 until a certain head of pressure builds up against ball 154. The increased head of pressure occurs by increasing the centrifugal force a factor, for example 50%, above the force used to achieve phase separation. Preferably, the speed of rotation is increased a corresponding amount. Since the serum and blood cells are relatively incompressible against wall 144, the increase in centrifugal force CF translates into an increased force in the direction of arrow 149, which overcomes spring constant $K_1$ of spring 160, and the valve opens. However, this is true only as long as enough serum or plasma remains in chamber 132 to push out aperture 156. When most of the serum or plasma has passed through the valve, the head of pressure occurring even at the increased speed of rotation, drops. As a result, valve 150 closes automatically even at the higher speeds of rotation.

In addition to the foregoing, container 100 preferably has the following features: Top wall 180 has a pressurizing aperture 182 covered with a puncturable seal 184, FIG. 4. Bottom wall 186 opposite to top wall 180 is provided with a dispensing aperture 188, FIG. 5, which can have any desired shape, preferably one that optimizes serum dispensing. Aperture 188 is positioned at the end of a passageway 190, such that it is located beyond the position, shown as "M", that the serum meniscus will occupy during spinning of container 100. Most preferably, passageway 190 is of capillary dimensions, to prevent meniscus M from advancing until aperture 182 is pressurized.

Thus, it is essential that container 100 be placed onto support 80 with the proper orientation, that is, with top wall 180 down so that dispensing aperture 188 is up. This insures that the heavier cell phase is pushed against baffles 148 during centrifuging.

Pressurizing of aperture 182 occurs at dispensing station 20, FIG. 1, when a pressurizing nozzle 200 is pushed, arrow 202, FIG. 4, through seal 184. Nozzle 200 is in turn connected to a controlled source of air pressure $\Delta P$, which can be any conventional source, for example, a piston. This pressure acts to force first the air pocket in front of meniscus M, FIG. 5, and then the serum, out of aperture 188. Control of the amount of $\Delta P$ ensures that the desired amount of serum is dispensed, as is conventional.

Figure 7:
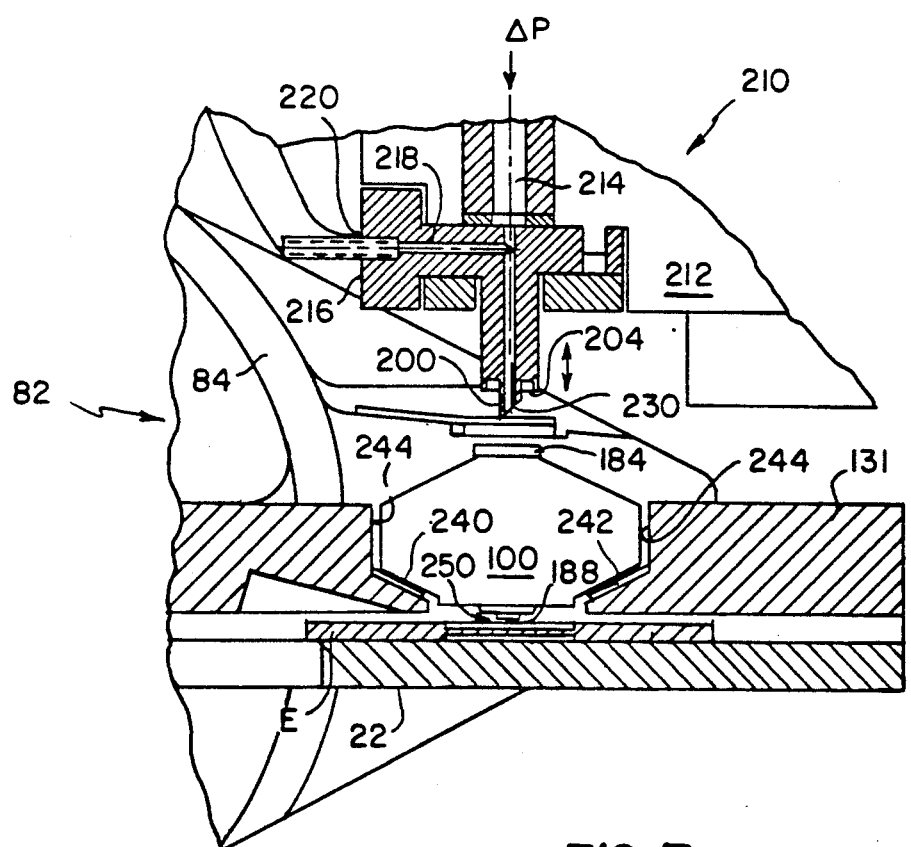
FIG. 7 is an elevational view taken in section generally along the line VII—VII of FIG. 1, with the test element E advanced into the dispensing station.

Referring to FIG. 7, the dispensing station thus comprises a pressurizing pump mechanism 210 having at the bottom thereof, nozzle 200. The pump mechanism comprises a housing 212 mounted for vertical movement by any conventional mechanism, e.g., rails (not shown). Pressurized air is supplied from a piston chamber 214 and motor-operated piston (not shown) that seals against a T-housing 216 that provides nozzle 200 as part of the "T". The other part of the "T" is a path 218 that leads to a vent 220 that can be used to normalize the pressure in chamber 214, if desired. As shown, nozzle 200 is preferably cut on a diagonal at 230, to make penetration of seal 184 more readily possible, on container 100. A sealing ring 204 is effective to seal around aperture 182, FIG. 4, after seal 184 is punctured.

Support 131 is preferably constructed, FIG. 7, with guide surfaces 240, 242 and side walls 244. These act to guide and support container 100 into position under pump mechanism 210 and above test element E on support 22. Most particularly, container 100 at aperture 188 is positioned spaced away from the test element a suitable serum-dispensing distance, for example, about 0.66 mm.

Figure 9:
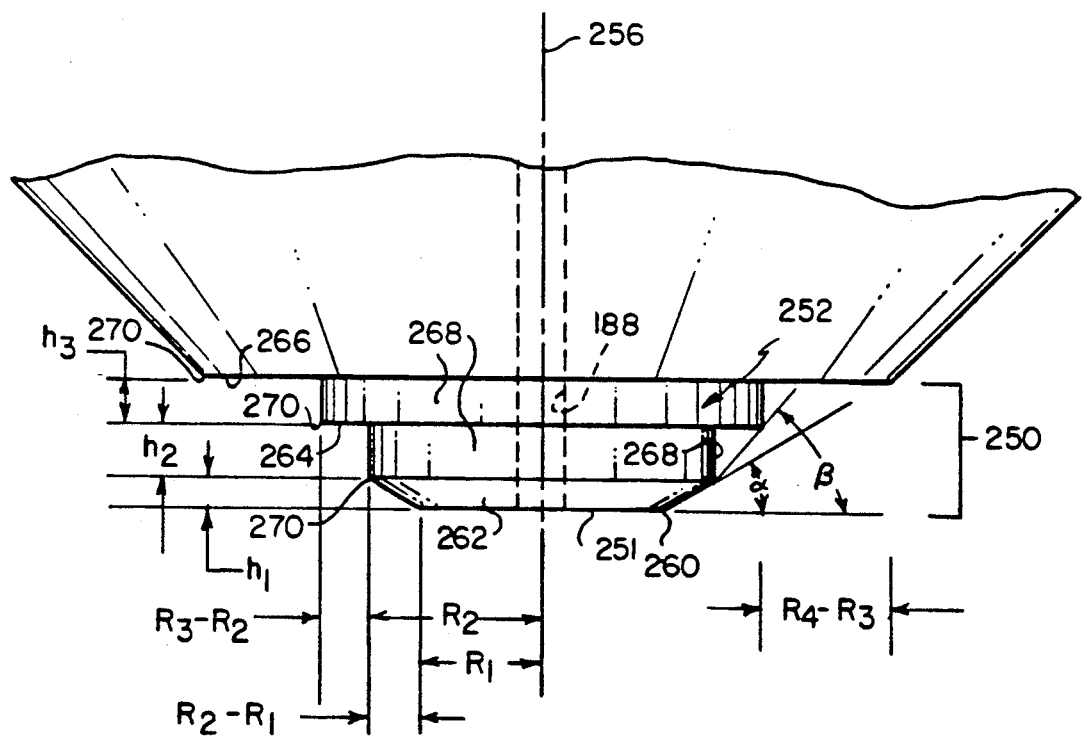
FIG. 9 is a fragmentary enlarged elevational view of the serum-dispensing nozzle shown in FIG. 7.

The nozzle 250 defining aperture 188 can have any desired shape. Most preferably, it is the shape described and claimed in commonly-owned U.S. Ser. No. 310,151 filed on Feb. 14, 1989 entitled "Liquid-Controlling Nozzle Geometry For Dispensers of Liquids". More specifically, FIG. 9, nozzle 250 includes a bottom surface 251 extending a distance, preferably a radius $R_1$, from axis 256. Preferably surface 251 is an annulus. Useful values of $R_1$ are set forth hereinafter. However, surface 251 is joined directly at edge 260, with a surface 262 inclined at an angle $\alpha$ to surface 251, the sign of angle $\alpha$ being such as to cause surfaces 251 and 262 to form a convex surface. Surface 262 is generally annular and extends to subtend a distance, preferably a difference radius $R_2-R_1$, from axis 256. As used herein "generally annular" is satisfied if the shape approximates an annulus. In addition, nozzle 250 features a series of lands 264 and 266 stepped back along axis 256, up the side of the nozzle. Each of these lands is preferably generally annular in shape and generally parallel to surface 251 and has a dimension, preferably a radius $R_3$ and $R_4$, respectively, from axis 256, so that the surface area of each land is a function of the difference in the two bounding radii, $R_N-R_{N-1}$, where N is 3 for land 264, and N is 4 for land 266. Each land is stepped back, preferably straight back, so as to be spaced, along axis 256, a distance of $h_2$ and $h_3$, respectively, from the adjacent surface closer to surface 251. (Distance $h_1$ for surface 262 is, of course, predetermined by the value of $R_1$ angle $\alpha$ and radius $R_2$.)

An important feature of lands 264 and 266 is that their outermost radii $R_3$ and $R_4$, respectively, give to the exterior surface of nozzle 250, an overall angle $\beta$, measured from the plane of surface 251, that is effective to give maximum drainage of liquid on the exterior of nozzle 250. Other important features are the recesses formed by the step in each land, and distances $h_2$ and $h_3$. That is, each step forms a gap in the overall cone shape suggested by angle $\beta$, with a step-back surface 268 providing distance $h_2$ and $h_3$, such gaps being effective to trap and break up any sheaths of liquid that can be left on the exterior of nozzle 250.

The selection of angle beta, and of the distances $h_2$ and $h_3$ as noted above, is useful in nozzle 250 because accidental perfusion might occur and these features help insure that nozzle 250 will still dispense accurately as expected, inspite of perfusion.

It will be recognized that the shape of lands 264 and 266 need only be roughly annular, in which case $R_N-R_{N-1}$ is not strictly speaking determined by subtracting radii. In cases where $R_N$ and $R_{N-1}$ are dimensions of a non-circular curve, the value of $R_N-R_{N-1}$ is simply the width of that land as it extends around stepback surface 268.

The following Table gives a list of preferred ranges, and of an exemplary "most preferred" value, for each of the aforementioned dimensions.

| Items | Dimensional Values | |
|---|---|---|
| | Range | Most Preferred |
| Angle $\alpha$ | 6°–30° | 12° |
| Angle $\beta$ | 40°–60° | 53° |
| radius $R_1$ | 0.057–0.076 cm | 0.063 cm |
| radius difference ($R_2-R_1$) | 0.013–0.13 cm | 0.063 cm |
| radius difference ($R_3-R_2$) | 0.013–0.13 cm | 0.076 cm |
| radius difference ($R_4-R_3$) | 0.013–0.13 cm | 0.1 cm |
| height $h_2$ | 0.035–0.08 cm | 0.05 cm |
| height $h_3$ | 0.02–0.05 cm | 0.04 cm |

Most preferably, each of the edges 270 created by the intersection of a surface such as land 264, 266, or surface 262, with the vertically-extending step-back surface 268, is relatively sharp, that is, has a radius of curvature not to exceed about 0.02 cm.

When pump mechanism 210 is advanced downward, nozzle 200 penetrates seal 184, and an increase of pressure $\Delta P$ in chamber 214 causes a quantity of serum, e.g., from 6 to 10 $\mu l$, to be dispensed from aperture 188 onto test element E.

It is not necessary that the chamber 164 of the container of FIG. 5 be shaped as shown. A reduction in collected volume can be achieved, without the risk of entrapped air, if the chamber is modified as shown in FIGS. 10–13. The details of this construction are described and claimed in the commonly-owned application entitled "Blood Collection Device with Reduced Serum Dispensing Volume and Integral Needle" cofiled herewith by R. L. Columbus.

Specifically, the serum tranfer chamber has been especially constructed to minimize the volume collection to no greater than 150 $\mu l$, while ensuring that no air entrapment occurs in that chamber. Thus, tube 330 is constructed with a chamber 332 for phase separation that has its long dimension l oriented perpendicular, not parallel, FIG. 11, to the direction of centrifugal force CF, arrow 334, and with a specially constructed valve 350. Chamber 332 is defined by a body member 333 having a blood intake end 336 and an opposite, serum-removal end 338. Chamber 332 extends from end 336 to delivery passageway 356. End 336 has an intake aperture 340 filled with a conventional septum 341, chamber 332 being either vented at 343 or evacuated due to attachment at 343 to an external vacuum source, to assist in blood intake. Aperture 340 allows entrance of whole blood via passageway 342 to chamber 332. The width "d" of chamber 332 is one of the shorter dimensions. Sidewall 344 of chamber 332 is the sidewall against which the heavier blood cells collect, whereas opposite sidewall 346 is adjacent the lighter serum fraction, during centrifugation.

As described previously, fixed porous mechanical means, such as baffles 348, can be positioned along wall 344 so as to be disposed in the blood cells. The plates of the baffles are inclined at an angle alpha that resists remixing forces when flow occurs out of chamber 332 in the direction of arrow 349. Preferably, this angle is a value that is between about 30° and about 120°, most preferably about 60°.

Alternatively, chemical agents can be used in place of baffles 348 to maintain the phase separation, for example cell agglutinating reagents.

Valve 350 is disposed at an end 352 of chamber 332 intermediate ends 336 and 338, positioned to draw off separated plasma or serum and lymphocytes, as described heretofore.

Serum or plasma exit passageway 362 is constructed adjacent seat 358, to carry off the liquid when valve 350 opens. Passageway 362 joins a second chamber or compartment 364 sized to receive substantially all the serum that exits chamber 332 via valve 350. It is this second chamber that is especially constructed to provide a reduced volume, as set forth hereinafter. It connects with two apertures—dispensing aperture 370 that is open to the atmosphere, and a pressurizing aperture 372, FIG. 10, that is temporarily sealed with a frangible seal 374. To avoid premature leakage of serum out of aperture 370, FIG. 11, that aperture is strategically located with respect to the meniscus of liquid that fills chamber 364 during transfer of serum through valve 350—it is downstream of meniscus $M_2$, as is readily achieved by locating aperture 370 closer to the spin axis 376 than is valve 350. In other words, distance $l_2$ is greater than distance l.

Figure 11:
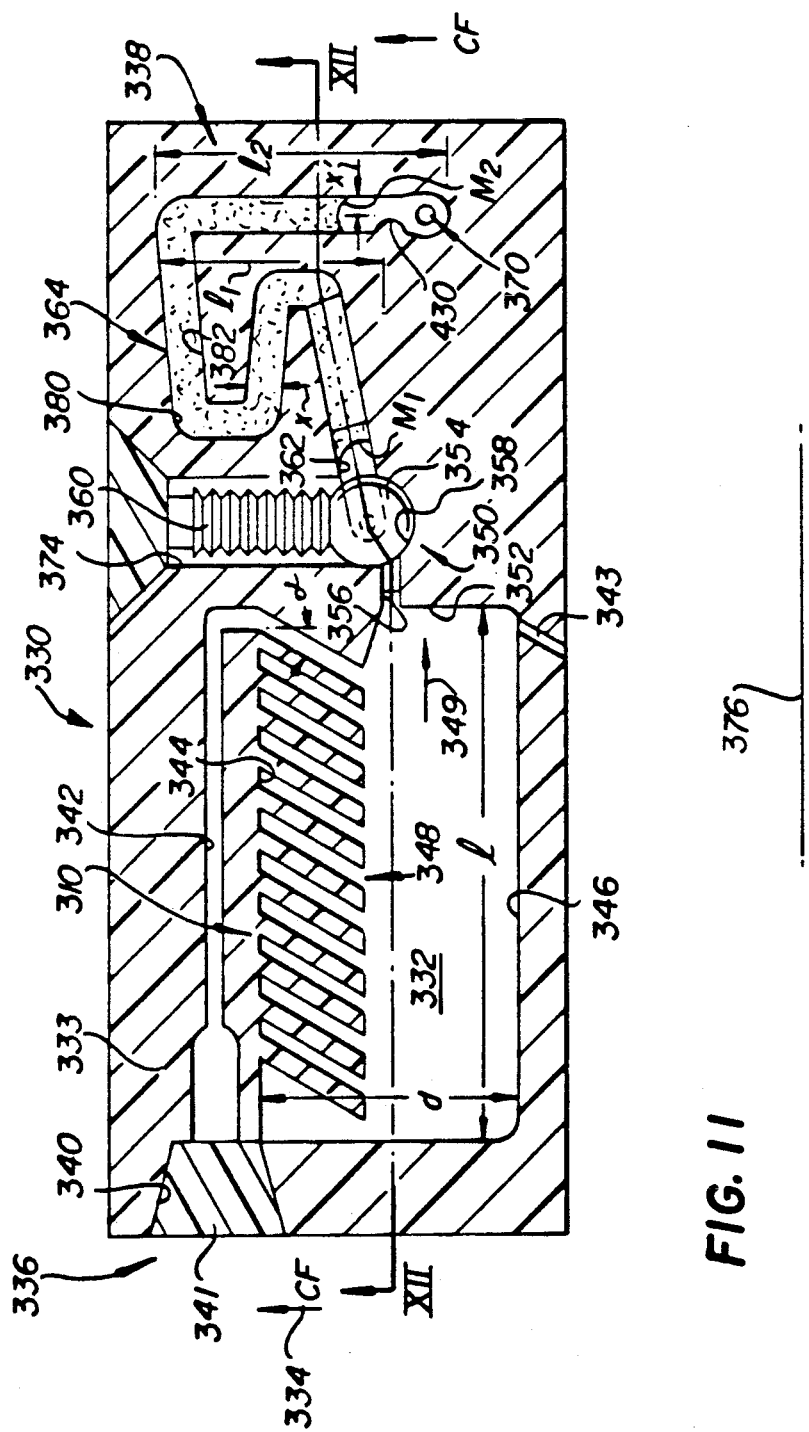
FIG. 11 is a section view taken generally along the line XI—XI of FIG. 10.

Chamber 364 is constructed to minimize serum volume so that it is less than about 150 $\mu l$, and at the same time keep serum that is transferred to the chamber, free of entrapped air. To this end, sidewalls 380 and 382 of chamber 364 are spaced apart a distance x throughout the transverse passage of the liquid (as seen in FIG. 11), that will ensure a weak capillary effect is maintained. This capillary effect is that which ensures that, once force CF is reduced to zero, the menisci $M_1$ and $M_2$ remain in place during normal handling of device 330. Otherwise, air entrapment is likely to occur. Distance x can be varied between about 0.1 mm and about 2 mm. Beyond these values, the capillary effect is likely to be either too strong or too weak, respectively, to give desired performance. Most preferably it is about 1 mm.

Regarding the height of chamber 364, and its three-dimensional shape other than dimension "x", these are not as critical. As is more clearly shown in FIG. 12, chamber 364 preferably is ramped to have an increased height "h" as the path extends away from valve 350. This height is limited only by the volume of serum that can be expected to flow from chamber 332. The three-dimensional, winding shape of chamber 364 is dictated by the fact that this results from it being folded about itself. The folding is necessary to achieve a total path length "p", FIG. 10, that will also provide the desired volume for the expected volume of serum. It will be readily appreciated that other fold geometries, besides that shown, can also be used.

Spring 360 preferably sits in a trap 374, FIG. 11. The function of the trap is to collect the few red blood cells that will gather prior to and during centrifuging, in passageway 356, allowing only desired serum, or plasma and lymphocytes, to pass into chamber 364.

Device 330 can be assembled as two plates, using a foil layer (not shown) to achieve a seal that will allow a vacuum to be drawn using vent 343, as described above.

Such a device 330 can be spun in any convenient centrifuge, not shown, where the long dimension l is generally parallel to the spin axis 376. Preferred spin radii are about 2.5 cm, although a wide variety can be used.

The method of phase separating, using device 330, will be readily apparent from the preceding discussion.

Once serum separation is achieved, a slight increase in force CF will produce, in the presence of a serum phase in chamber 332, an increased hydrostatic force in the direction of arrow 349, as described for previous embodiments. This in turn will unseat the ball valve. Serum will thus flow into chamber 362 until there remains no more liquid (serum) to push against the valve, and the valve closes. At this time, the menisci of the serum in chamber 364 will be at $M_1$ and $M_2$, thus leaving dispensing aperture 370 dry. In fact, the menisci remain at these locations even after force CF is reduced to zero, as the weak capillary attraction provided by side walls 380 and 382 will retain the liquid as shown. That is, the seal of the ball valve insures a vacuum is created to hold the column of serum in place.

Thereafter, seal 378, FIGS. 10 and 13, is pierced by a source of compressed air, which can be any type, which applies a pressure $\Delta P$ to aperture 372, FIG. 13. This in turn is effective to dispense fractions of the serum out aperture 370.

As shown in FIG. 13, seal 378 is mounted on the exterior of device 330. Alternatively, however, it can be mounted in a recess within the device, FIG. 14. That is, aperture 372 can have seal 378 secured within the aperture. In such an arrangement, aperture 372 is preferably enlarged at the surface of device 330 to form an annular recessed surface 391 used as a sealing surface. That is, a pressurizing source, shown in phantom, can be moved, arrow 393, so as to seat onto surface 391 while at the same time puncturing seal 378.

Because Meniscus $M_2$ is not already at aperture 370 when dispensing is to start, it is desirable to provide means for detecting the presence of meniscus $M_2$ at some predetermined location along path "p" before it encounters the aperture. The reason is that patients' hemocrits vary from sample to sample to sample. Hence, the exact location of meniscus $M_2$ at its upstream location (from aperture 370) cannot be predicted. As a result, the amount of pressurizing needed just to get meniscus $M_2$ to the aperture, is undetermined. The solution is readily achieved as follows:

A protrusion 430, FIG. 11, extends from at least one of walls 380 and 382, the full height of chamber 364, FIG. 13. This protrusion narrows the passageway of liquid flowing from the first location of meniscus $M_2$ to aperture 370, by an amount $(x-x^1)$ that produces a pressure increase when meniscus $M_2$ encounters it. To be detectable, the pressure increase need only be the amount of at least about 0.1 inch of water (about 0.025 kPa). The detection of such a pressure increase, due to the increased resistance, is readily achieved by a pressure transducer used with the pressurizing means (not shown). The exact amount of the extension of protrusion 430 depends upon the sensitivity of such pressure transducer. Preferably, that extension is about 0.025 cm. It can be as small as about 0.013 cm and as large as about 0.076 cm.

Alternatively, not shown, two opposing protrusions from both of the sidewalls can be used, in which case each protrusion extends only about one-half of $(x-x^1)$.

The shape of the protrusion 430 is not critical—it can be rounded or have a sharp corner.

The exact location of protrusion 430 along path "p" is also not crucial, so long as its location is known and represents a number of half-steps of a pressurizing motor needed to move the meniscus $M_2$ from the protrusion to aperture 370. Preferably, protrusion 430 is adjacent aperture 370, and most preferably, closely adjacent as shown, FIG. 11.

The invention has been described in detail with particular reference to preferred embodiments thereof, but it will be understood that variations and modifications can be effected within the spirit and scope of the invention.

What is claimed is:

1. In a blood analyzer comprising an incubator, a test element support, a serum dispensing station positioned adjacent to the incubator to dispense serum onto a test element disposed on said support, and means for moving a test element spotted with the dispensed serum from said dispensing station into said incubator:

the improvement wherein the analyzer further comprises a centrifuge disposed adjacent to said dispensing station and separate from said incubator, said centrifuge including a station for holding a container of whole blood, a spin axis, and means for mounting said station for spinning about said axis to separate serum from blood cells, means for moving a spun container from said centrifuge station to said dispensing station at a location spaced from said support, and further including means at said dispensing station cooperating with means in said container for dispensing serum from said container directly onto a test element on said support.

2. An analyzer as defined in claim 1, wherein said spin axis of said centrifuge is disposed in a horizontal plane.

3. An analyzer as defined in claim 1 or 2, wherein said moving means comprise a transfer mechanism for horizontally moving said spun container out of said centrifuge station to said dispensing station.

4. An analyzer as defined in claim 1 or 2, and further including means for moving a container of whole blood horizontally from a first position in the analyzer into a second position in a station in said centrifuge.

5. An analyzer as defined in claim 1 or 2, wherein said dispensing station includes means for penetrating and sealing against said container, and means for pressurizing the interior of said container when said penetrating and sealing means is in contact with said container.

6. An analyzer as defined in claim 1 or 2, and in combination therewith, a container for separating serum from whole blood by spinning in said centrifuge, said container having a first chamber, a second chamber and flow means allowing selective liquid flow of serum from said first chamber to said second chamber, said flow means including a valve means for controlling flow between said chambers, said second chamber including a dispensing aperture and having a volume no larger than about 150 µl that is constructed to form a path extending in three dimensions from said flow means to said dispensing aperture, the sidewalls of said second chamber being spaced apart a distance no greater than that which provides a weak capillary effect, to insure that liquid flow into said second chamber occurs without air entrapment.

* * * * *